United States Patent
Chanduszko et al.

(10) Patent No.: US 7,220,265 B2
(45) Date of Patent: May 22, 2007

(54) PATENT FORAMEN OVALE (PFO) CLOSURE METHOD AND DEVICE

(75) Inventors: Andrzej J. Chanduszko, South Boston, MA (US); Steven W. Opolski, Carlisle, MA (US); Carol A. Ryan, Melrose, MA (US)

(73) Assignee: NMT Medical, Inc., Boston, MA (US)

( * ) Notice: Subject to any disclaimer, the term of this patent is extended or adjusted under 35 U.S.C. 154(b) by 720 days.

(21) Appl. No.: 10/341,802

(22) Filed: Jan. 14, 2003

(65) Prior Publication Data

US 2003/0144694 A1 Jul. 31, 2003

Related U.S. Application Data

(60) Provisional application No. 60/347,336, filed on Jan. 14, 2002.

(51) Int. Cl.
*A61B 17/10* (2006.01)
*A61B 17/08* (2006.01)

(52) U.S. Cl. .................. 606/139; 606/151
(58) Field of Classification Search ........ 606/139, 606/151
See application file for complete search history.

(56) References Cited

U.S. PATENT DOCUMENTS

| | | |
|---|---|---|
| 3,874,388 A | 4/1975 | King et al. |
| 3,875,648 A | 4/1975 | Bone |
| 4,006,747 A | 2/1977 | Kronenthal et al. |
| 4,007,743 A | 2/1977 | Blake |
| 4,425,908 A | 1/1984 | Simon ............... 128/1 |
| 4,696,300 A | 9/1987 | Anderson |
| 4,710,192 A | 12/1987 | Liotta et al. |
| 4,836,204 A | 6/1989 | Landymore et al. |
| 4,902,508 A | 2/1990 | Badylak et al. |
| 4,915,107 A | 4/1990 | Rebuffat et al. |
| 4,917,089 A | 4/1990 | Sideris |
| 4,956,178 A | 9/1990 | Badylak et al. |
| 5,021,059 A | 6/1991 | Kensey et al. ............. 606/213 |
| 5,037,433 A | 8/1991 | Wilk et al. |
| 5,041,129 A | 8/1991 | Hayhurst et al. |
| 5,108,420 A | 4/1992 | Marks |

(Continued)

FOREIGN PATENT DOCUMENTS

EP 1 013 227 6/2000

(Continued)

OTHER PUBLICATIONS

Nat'l Aeronautics and Space Administration, "55-Nitinol—The Alloy with a Memory: Its Physical Metallurgy, Properties, and Applications," A Report, pp. 24-25.

(Continued)

*Primary Examiner*—Michael J. Hayes
*Assistant Examiner*—L. Bachman
(74) *Attorney, Agent, or Firm*—Wilmer Cutler Pickering Hale and Dorr LLP (57) ABSTRACT

The present invention provides methods and devices for closing two overlapping layers of tissue in a mammalian heart, for example a patent foramen ovale (PFO). The closure devices may take a number of different forms and may be retrievable. In some embodiments, the closure devices may be delivered with a catheter capable of puncturing mammalian tissue.

29 Claims, 10 Drawing Sheets

U.S. PATENT DOCUMENTS

| | | | |
|---|---|---|---|
| 5,171,259 A | 12/1992 | Inoue | |
| 5,192,301 A | 3/1993 | Kamiya et al. | |
| 5,222,974 A | 6/1993 | Kensey et al. | 606/213 |
| 5,236,440 A | 8/1993 | Hlavacek | |
| 5,257,637 A | 11/1993 | El Gazayerli | |
| 5,275,826 A | 1/1994 | Badylak et al. | |
| 5,282,827 A | 2/1994 | Kensey et al. | 606/215 |
| 5,284,488 A | 2/1994 | Sideris | |
| 5,304,184 A | 4/1994 | Hathaway et al. | |
| 5,312,341 A | 5/1994 | Turi | |
| 5,312,435 A | 5/1994 | Nash et al. | 606/213 |
| 5,334,217 A | 8/1994 | Das | 606/213 |
| 5,354,308 A | 10/1994 | Simon et al. | 606/198 |
| 5,411,481 A | 5/1995 | Allen et al. | |
| 5,413,584 A | 5/1995 | Schulze | |
| 5,417,699 A | 5/1995 | Klein et al. | |
| 5,425,744 A | 6/1995 | Fagan et al. | |
| 5,433,727 A | 7/1995 | Sideris | |
| 5,451,235 A | 9/1995 | Lock et al. | |
| 5,478,353 A | 12/1995 | Yoon | |
| 5,480,424 A | 1/1996 | Cox | |
| 5,486,193 A | 1/1996 | Bourne et al. | |
| 5,507,811 A | 4/1996 | Koike et al. | |
| 5,540,712 A | 7/1996 | Kleshinski et al. | 606/198 |
| 5,577,299 A | 11/1996 | Thompson et al. | |
| 5,601,571 A | 2/1997 | Moss | |
| 5,618,311 A | 4/1997 | Gryskiewicz | |
| 5,620,461 A | 4/1997 | Muijs Van De Moer et al. | |
| 5,626,599 A | 5/1997 | Bourne et al. | |
| 5,634,936 A | 6/1997 | Linden et al. | |
| 5,649,950 A | 7/1997 | Bourne et al. | |
| 5,683,411 A | 11/1997 | Kavteladze et al. | |
| 5,693,085 A | 12/1997 | Buirge et al. | |
| 5,702,421 A | 12/1997 | Schneidt | |
| 5,709,707 A | 1/1998 | Lock et al. | |
| 5,720,754 A | 2/1998 | Middleman et al. | 606/127 |
| 5,725,552 A | 3/1998 | Kotula et al. | |
| 5,733,294 A | 3/1998 | Forber et al. | |
| 5,733,337 A | 3/1998 | Carr, Jr. et al. | |
| 5,741,297 A | 4/1998 | Simon | |
| 5,776,162 A | 7/1998 | Kleshinski | 606/198 |
| 5,797,960 A | 8/1998 | Stevens et al. | |
| 5,800,516 A | 9/1998 | Fine et al. | |
| 5,810,884 A | 9/1998 | Kim | 606/213 |
| 5,823,956 A | 10/1998 | Roth et al. | |
| 5,829,447 A | 11/1998 | Stevens et al. | |
| 5,853,422 A | 12/1998 | Huebsch et al. | |
| 5,855,614 A | 1/1999 | Stevens et al. | |
| 5,861,003 A | 1/1999 | Latson et al. | 606/213 |
| 5,865,791 A | 2/1999 | Whayne et al. | |
| 5,879,366 A | 3/1999 | Shaw et al. | |
| 5,893,856 A | 4/1999 | Jacob et al. | |
| 5,902,319 A | 5/1999 | Daley | |
| 5,904,703 A | 5/1999 | Gilson | |
| 5,919,200 A | 7/1999 | Stambaugh et al. | |
| 5,924,424 A | 7/1999 | Stevens et al. | |
| 5,928,250 A | 7/1999 | Koike et al. | |
| 5,944,738 A | 8/1999 | Amplatz et al. | |
| 5,955,110 A | 9/1999 | Patel et al. | |
| 5,976,174 A | 11/1999 | Ruiz | |
| 5,989,268 A | 11/1999 | Pugsley, Jr. et al. | |
| 5,993,475 A | 11/1999 | Lin et al. | 606/213 |
| 5,993,844 A | 11/1999 | Abraham et al. | |
| 5,997,575 A | 12/1999 | Whitson et al. | |
| 6,010,517 A | 1/2000 | Baccaro | 606/151 |
| 6,024,756 A | 2/2000 | Huebsch et al. | |
| 6,030,007 A | 2/2000 | Bassily et al. | |
| 6,056,760 A | 5/2000 | Koike et al. | |
| 6,077,291 A | 6/2000 | Das | 606/213 |
| 6,079,414 A | 6/2000 | Roth | |
| 6,080,182 A | 6/2000 | Shaw et al. | |
| 6,096,347 A | 8/2000 | Geddes et al. | |
| 6,106,913 A | 8/2000 | Scardino et al. | |
| 6,113,609 A | 9/2000 | Adams | 606/139 |
| 6,117,159 A | 9/2000 | Huebsch et al. | |
| 6,126,686 A | 10/2000 | Badylak et al. | |
| 6,132,438 A | 10/2000 | Fleischman et al. | 606/139 |
| 6,152,144 A | 11/2000 | Lesh et al. | |
| 6,165,183 A | 12/2000 | Kuehn et al. | 606/139 |
| 6,165,204 A | 12/2000 | Levinson et al. | |
| 6,171,329 B1 | 1/2001 | Shaw et al. | |
| 6,174,322 B1 | 1/2001 | Schneidt | |
| 6,187,039 B1 | 2/2001 | Hiles et al. | |
| 6,206,895 B1 | 3/2001 | Levinson | |
| 6,206,907 B1 | 3/2001 | Marino et al. | |
| 6,214,029 B1 | 4/2001 | Thill et al. | |
| 6,217,590 B1 | 4/2001 | Levinson | |
| 6,221,092 B1 | 4/2001 | Koike et al. | |
| 6,228,097 B1 | 5/2001 | Levinson et al. | |
| 6,231,561 B1 * | 5/2001 | Frazier et al. | 604/500 |
| 6,245,080 B1 | 6/2001 | Levinson | |
| 6,265,333 B1 | 7/2001 | Dzenis et al. | |
| 6,270,515 B1 | 8/2001 | Linden et al. | |
| 6,277,138 B1 | 8/2001 | Levinson et al. | |
| 6,277,139 B1 | 8/2001 | Levinson et al. | |
| 6,287,317 B1 | 9/2001 | Makower et al. | |
| 6,290,674 B1 * | 9/2001 | Roue et al. | 604/107 |
| 6,306,150 B1 | 10/2001 | Levinson | |
| 6,306,424 B1 | 10/2001 | Vyakarnam et al. | |
| 6,312,446 B1 | 11/2001 | Huebsch et al. | |
| 6,319,263 B1 | 11/2001 | Levinson | |
| 6,322,548 B1 | 11/2001 | Payne et al. | |
| 6,328,727 B1 | 12/2001 | Frazier et al. | |
| 6,334,872 B1 | 1/2002 | Termin et al. | |
| 6,342,064 B1 | 1/2002 | Koike et al. | |
| 6,344,049 B1 | 2/2002 | Levinson et al. | |
| 6,346,074 B1 | 2/2002 | Roth | |
| 6,348,041 B1 | 2/2002 | Klint | 600/585 |
| 6,352,552 B1 | 3/2002 | Levinson et al. | |
| 6,355,052 B1 | 3/2002 | Neuss et al. | |
| 6,364,853 B1 | 4/2002 | French et al. | |
| 6,375,625 B1 | 4/2002 | French et al. | |
| 6,375,671 B1 | 4/2002 | Kobayashi et al. | |
| 6,379,342 B1 | 4/2002 | Levinson | |
| 6,379,368 B1 | 4/2002 | Corcoran et al. | |
| 6,387,104 B1 | 5/2002 | Pugsley, Jr. et al. | 606/139 |
| 6,398,796 B2 | 6/2002 | Levinson | |
| 6,402,772 B1 | 6/2002 | Amplatz et al. | |
| 6,419,669 B1 | 7/2002 | Frazier et al. | |
| 6,436,088 B2 | 8/2002 | Frazier et al. | |
| 6,440,152 B1 | 8/2002 | Gainor et al. | 606/213 |
| 6,460,749 B1 | 10/2002 | Levinson et al. | |
| 6,482,224 B1 | 11/2002 | Michler et al. | |
| 6,488,706 B1 | 12/2002 | Solymar | 623/3.1 |
| 6,494,888 B1 | 12/2002 | Laufer et al. | 606/153 |
| 6,551,303 B1 | 4/2003 | Van Tassel et al. | |
| 6,551,344 B2 | 4/2003 | Thill | |
| 6,596,013 B2 | 7/2003 | Yang et al. | |
| 6,623,508 B2 | 9/2003 | Shaw et al. | |
| 6,623,518 B2 | 9/2003 | Thompson et al. | |
| 6,666,861 B1 | 12/2003 | Grabek | |
| 6,712,804 B2 | 3/2004 | Roue et al. | |
| 6,712,836 B1 | 3/2004 | Berg et al. | |
| 2001/0014800 A1 | 8/2001 | Frazier et al. | |
| 2001/0034537 A1 | 10/2001 | Shaw et al. | 606/213 |
| 2001/0037129 A1 | 11/2001 | Thill | 606/213 |
| 2001/0039435 A1 | 11/2001 | Roue et al. | |
| 2001/0041914 A1 | 11/2001 | Frazier et al. | |
| 2001/0041915 A1 | 11/2001 | Roue et al. | |
| 2001/0044639 A1 | 11/2001 | Levinson | |
| 2001/0049492 A1 | 12/2001 | Frazier et al. | 604/104 |
| 2002/0010481 A1 | 1/2002 | Jayaraman | 606/151 |
| 2002/0019648 A1 | 2/2002 | Akerfeldt et al. | |
| 2002/0026208 A1 | 2/2002 | Roe et al. | |

| | | |
|---|---|---|
| 2002/0029048 A1 | 3/2002 | Miller |
| 2002/0032462 A1 | 3/2002 | Houser et al. |
| 2002/0035374 A1 | 3/2002 | Borillo et al. |
| 2002/0043307 A1 | 4/2002 | Ishida et al. ............... 148/411 |
| 2002/0052572 A1 | 5/2002 | Franco et al. |
| 2002/0077555 A1 | 6/2002 | Schwartz .................... 600/486 |
| 2002/0096183 A1 | 7/2002 | Stevens et al. |
| 2002/0099389 A1 | 7/2002 | Michler et al. |
| 2002/0107531 A1 | 8/2002 | Schreck et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. ............ 128/831 |
| 2002/0169377 A1 | 11/2002 | Khairkhahan et al. |
| 2002/0183786 A1 | 12/2002 | Girton ........................ 606/213 |
| 2002/0183787 A1 | 12/2002 | Wahr et al. .................. 606/213 |
| 2002/0183823 A1 | 12/2002 | Pappu |
| 2002/0198563 A1 | 12/2002 | Gainor et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0059640 A1 | 3/2003 | Marton et al. .............. 428/544 |
| 2003/0065379 A1 | 4/2003 | Babbas et al. |
| 2003/0100920 A1 | 5/2003 | Akin et al. |
| 2003/0139819 A1 | 7/2003 | Beer et al. |
| 2003/0191495 A1 | 10/2003 | Ryan et al. |
| 2003/0195530 A1 | 10/2003 | Thill |
| 2003/0204203 A1 | 10/2003 | Khairkhahan et al. |
| 2004/0044361 A1 | 3/2004 | Franzier et al. |
| 2004/0210301 A1 | 10/2004 | Obermiller |

FOREIGN PATENT DOCUMENTS

| | | |
|---|---|---|
| EP | 1 046 375 | 10/2000 |
| EP | 1 222 897 | 7/2002 |
| WO | WO 96/25179 | 8/1996 |
| WO | WO 96/31157 | 10/1996 |
| WO | WO 00/27292 | 5/2000 |
| WO | WO 00/44428 | 8/2000 |
| WO | WO 01/49185 | 7/2001 |
| WO | WO 02/24106 | 3/2002 |
| WO | WO 03/077733 | 9/2003 |

OTHER PUBLICATIONS

Kimura, A., et al., "Effects of Neutron Irradiation on the Transformation Behavior in Ti-Ni Alloys," Abstract, Proceedings of the Int'l Conf. On Mariensitic Transformations (1992) pp. 935-940.

Ramanathan, G., et al., "Experimental and Computational Methods for Shape Memory Alloys," 15$^{th}$ ASCE Engineering Mechanics Conf., Jun. 2-5, 2003.

Shabalovskaya, S., "Surface, corrosion and biocompatibility aspects of Nitinol as an implant material," Bio-Medical materials and Engineering, (2002) vol. 12, pp. 69-109.

Uchil, J. "Shape Memory Alloys—Characterization Techniques," Pramana—Journal of Physics, (2002) vol. 58, Nos. 5 & 6, pp. 1131-1139.

Stöckel, "Nitinol Medical Devices and Implants," SMST-2000 Conference Proceedings, 2001, pp. 531-541.

SMST-2000, "Proceedings of the International Conference on Shape Memory and Superlastic Technologies," Apr. 30 to May 4, 2000, Asilomar Conference Center.

Ruiz et al. "The Puncture Technique: A New Method for Transcatheter Closure of Patent Foramen Ovale," Catheterization and Cardiovascular Interventions 53, Wiley-Liss, Inc., 2001, pp. 369-372.

International Search Report, International Application No. PCT/US03/17390, mailed on Oct. 6, 2003, 4 pgs.

* cited by examiner

Puncture Site through Septum Primum

PATENT FORAMEN OVALE (PFO) CLOSURE METHOD AND DEVICE

BACKGROUND OF THE INVENTION

Figure 1:
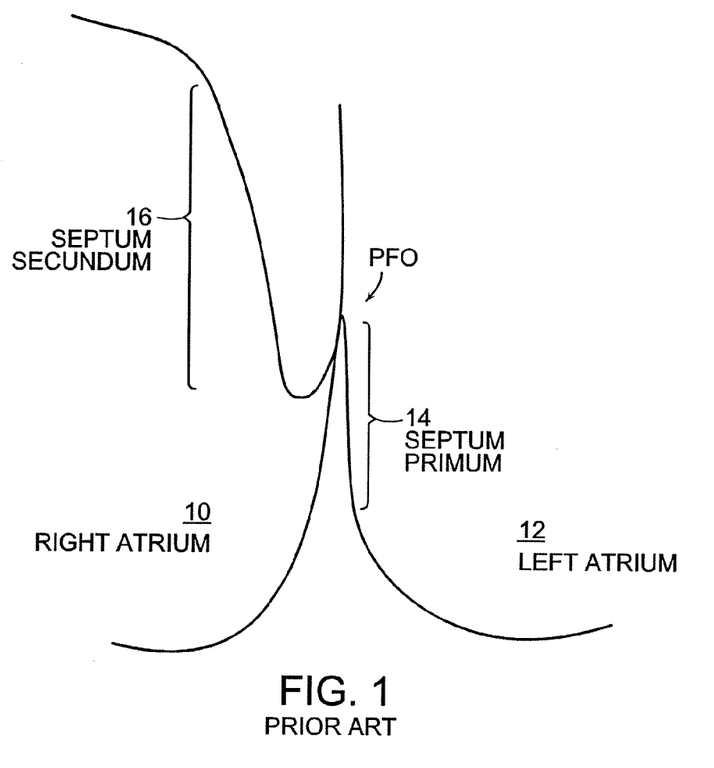
FIG. 1 is a diagrammatic sectional view of a Patent Foramen Ovale (PFO)

A patent foramen ovale (PFO) as shown in FIG. 1, is a persistent, one-way, usually flap-like opening in the wall between the right atrium 10 and left atrium 12 of the heart. Since left atrial (LA) pressure is normally higher than right atrial (RA) pressure, the flap typically stays closed. Under certain conditions, however, RA pressure can exceed LA pressure creating the possibility for right to left shunting that can allow blood clots to enter the systemic circulation. In utero, the foramen ovale serves as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a PFO has been shown to persist in a number of adults.

The cause of ischemic stroke remains cryptogenic (of unknown origin) in approximately 40% of cases. Especially in young patients, paradoxical embolism via a PFO is considered in the diagnosis. While there is currently no proof for a cause-effect relationship, many studies have confirmed a strong association between the presence of a PFO and the risk for paradoxical embolism or stroke. In addition, there is good evidence that patients with PFO and paradoxical embolism are at increased risk for future, recurrent cerebrovascular events.

The presence of a PFO has no therapeutic consequence in otherwise healthy adults. In contrast, patients suffering a stroke or transient ischemic attack (TIA) in the presence of a PFO and without another cause of ischemic stroke are considered for prophylactic medical therapy to reduce the risk of a recurrent embolic event. These patients are commonly treated with oral anticoagulants, which have the potential for adverse side effects, such as hemorrhaging, hematoma, and interactions with a variety of other drugs.

In certain cases, such as when anticoagulation is contraindicated, surgery may be used to close the PFO. To suture a PFO closed requires attachment of septum secundum to septum primum with either an interrupted or a continuous stitch, which is the common way a surgeon shuts the PFO under direct visualization.

Nonsurgical closure of PFOs has become possible with the advent of umbrella devices and a variety of other similar mechanical closure designs, developed initially for percutaneous closure of atrial septal defects (ASD). These devices allow patients to avoid the potential side effects often associated with anticoagulation therapies.

Currently available designs of septal closure devices, however, present such drawbacks as technical complexity of implantation procedure, high complication rates (thrombus, fractures, conduction system disturbances, perforations, residual leaks), high septal profile, large masses of foreign material, and lack of anatomic conformability especially to the PFO flap-like anatomy, as most were originally designed to close ASD's, which are true holes. Additionally, some septal closure devices are complex to manufacture, which can result in lack of consistency in product performance.

SUMMARY OF THE INVENTION

In one aspect, the present invention provides a method of closing two overlapping layers of tissue in a mammalian heart, e.g., a patent foramen ovale (PFO), using a closure device that applies a compressive force to at least one of the layers of tissue. The closure device may be retrievable, such that it may be removed after a period of time sufficient to allow the overlapping layers of tissue to fuse together. If necessary to sufficiently close the length of the layers of tissue, multiple closure devices may be administered. The closure devices may be delivered with a catheter capable of puncturing mammalian tissue in at least one location.

The closure device of the present invention may take a number of different forms. For example, the closure device may have first and second ends, both of which may be capable of puncturing mammalian tissue. The device may be a structure such as a ring with a gap, a folded ring, at least one grappling hook member joined to at least one curved arm by a joinder member, opposed grappling hook members joined by a central connecting member, a grappling hook member and a central connecting member, or a closure device anchor joined to a structure of sufficient diameter to hold the device in place against the overlapping layers of tissue. In some embodiments of the present invention, the closure device is sized and shaped such that it extends from septum secundum in the left atrium, into the left atrium, through septum primum, into the right atrium, and to septum secundum in the right atrium. Some retrievable devices include elongate tethers to facilitate their removal. Each of these devices has certain advantages, and one skilled in the art will be capable of selecting the device appropriate for a given application.

The ends of the closure device may also take a number of different forms. For example, at least one end may form a disc or a closure device anchor, such as a coil, hook, or corkscrew. These end structures help to maintain the device in place. One of the ends, for example the second end, may take the form of a knot or a structure similarly capable of holding the device in place and applying a sufficient compressive force to the overlapping layers of tissue. In some embodiments, the end structure may be adjusted to alter the compressive force applied to the overlapping layers of tissue. As previously mentioned, either or both of the first and second ends may be capable of puncturing mammalian tissue. In some embodiments, the first end of the device is a septal puncture needle.

The closure device may be formed of any of several materials, such as flexible polymer materials, bioabsorbable materials, shape memory materials, metals, noble metals, or swellable foams. In particular embodiments, the device includes nitinol. Some of the devices are formed from a single piece of material, while others are formed from multiple pieces of material joined together.

Some closure devices according to the present invention are intended to puncture septum primum upon insertion into the heart. For example, such a device may be inserted into the right atrium of the heart and puncture septum primum to enter the left atrium of the heart. At this point, the first end of the device may simply be deployed into the left atrium, or the first end of the device may be deployed into the left atrium and at least partially puncture septum secundum. In those embodiments where the first end of the device at least partially punctures septum secundum, the first end may be embedded in septum secundum or may completely puncture septum secundum such that the first end extends into the right atrium. The second end of the device may then be positioned against septum secundum in the right atrium, thereby providing a compressive force to the septal tissues. In other embodiments, the second end is also positioned in the left atrium while another portion of the device, such as a fold, is positioned in the right atrium, thereby compressing the septal tissues between the device.

Alternatively, some closure devices according to the present invention are intended to be inserted between the overlapping layers of tissue, e.g. through the PFO tunnel, to enter the left atrium. In these embodiments, the first end of the device is then deployed in the left atrium and the second end of the device is deployed in the right atrium, thereby providing a compressive force to the septal tissue. As discussed above, at least one of the ends of the device may partially puncture septum secundum.

These and other features will become readily apparent from the following detailed description wherein embodiments of the invention are shown and described by way of illustration.

DESCRIPTION OF THE PREFERRED EMBODIMENTS

Figure 2:
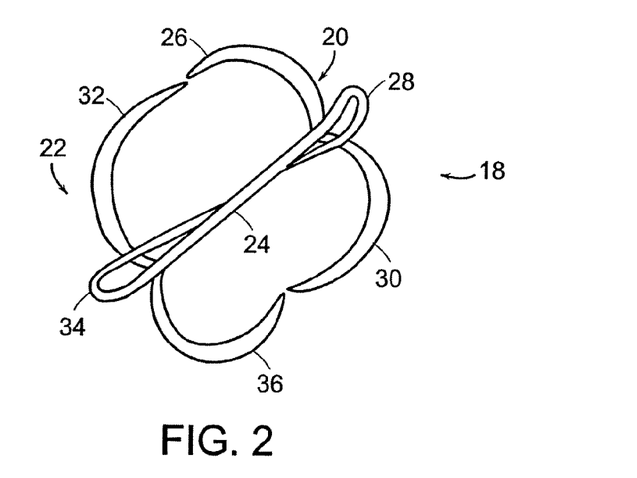
FIG. 2 is a view in side elevation of the PFO closure device with mechanical anchors of the present invention.
Figure 3A:
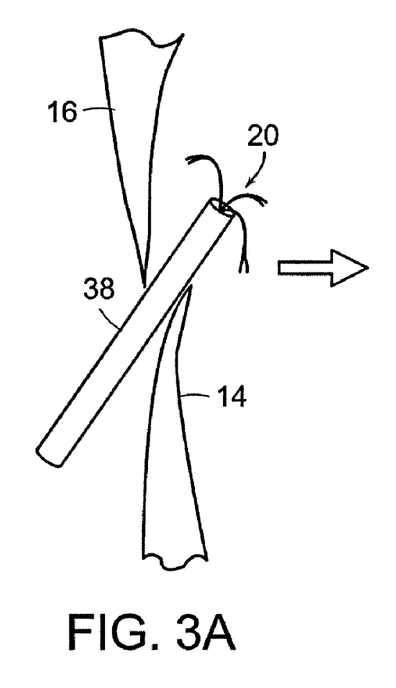
FIGS. 3a, 3b and 3c illustrate the steps in the deployment of the PFO closure device of FIG. 2.
Figure 3B:
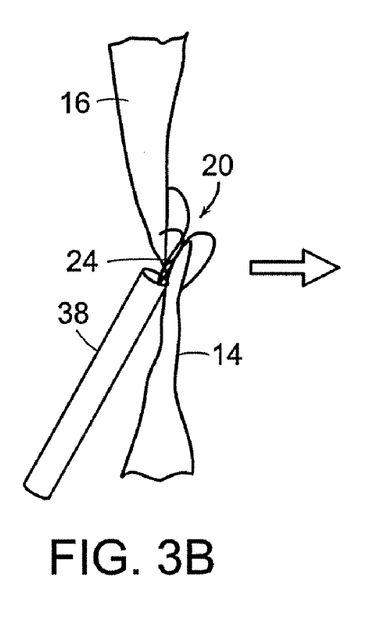
Figure 3C:
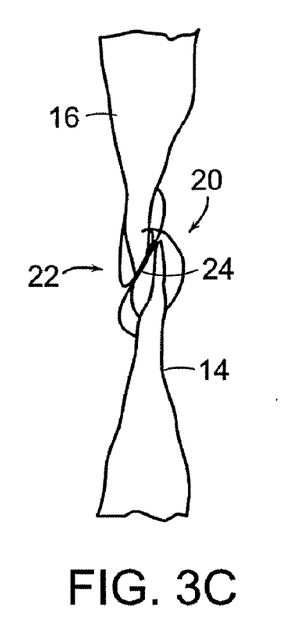

Referring to FIGS. 2 and 3, a PFO closure device with mechanical anchors indicated generally at 18 includes opposed grappling hook members 20 and 22 connected by a central connecting member 24. When the PFO closure device 18 is deployed, the grappling hook members 20 and 22 each include two or more curved hooks. In FIGS. 2 and 3, three curved hooks 26, 28 and 30 form the grappling hook member 20 and three curved hooks 32, 34 and 36 form the grappling hook member 22. As shown in FIG. 2, the grappling hooks 26, 28, 30, 32, 34, and 36 extend radially from the central connecting member 24. The grappling hooks of grappling hook members 20 and 22 have the same geometry but are rotated such that each grappling hook of grappling hook member 20 is situated precisely between two opposed grappling hooks of grappling hook member 22. The angle between any two grappling hooks of grappling hook members 20 and 22 may be determined by the formula 360°/(number of hooks per grappling hook member). To fit within a catheter, these hooks may all be straightened outwardly and compressed to lie along the longitudinal axis of the central connecting member 24. In this form, the PFO closure device extends longitudinally within a catheter 38.

To deploy the PFO closure device 18, the catheter 38 is inserted from the right atrium 10 through the PFO tunnel, i.e. between septum primum 14 and septum secundum 16, into the left atrium 12. As shown in FIG. 3a, the grappling hook member 20 is deployed into the left atrium. Next, as shown in FIG. 3b, the catheter 38 is drawn back into the right atrium and the grappling hooks 26, 28 and 30 are drawn back and embedded in the left sides of septum primum and septum secundum. The central connecting member 24 extends at an angle through the PFO tunnel permitting septum primum and septum secundum to be drawn to the closed position and secured by the grappling hooks 26, 28 and 30. Finally, as shown in FIG. 3c, the catheter 38 is drawn back to permit the grappling hook member 22 to deploy, and grappling hooks 32, 34 and 36 pierce the right side of septum primum and septum secundum.

The grappling hook members 20 and 22 may be formed of flexible, spring-like, bioabsorbable polymer material so as to permit movement from the compressed straight shape to the curved hook shapes following deployment from the catheter 38. The central connecting member 24 may also be formed of bioabsorbable material, such as an absorbable suture material, so the device will ultimately leave no foreign substance in either atrium. Alternatively, the grappling hook members 20 and 22 may be formed of spring metal or of a shape memory material, such as nitinol. When the PFO closure device is not formed of bioabsorbable material, it is possible to form the device with only the grappling hook member 20 and a central connecting member 24 so that the device is repositionable and retrievable. When the device is made of a bioabsorbable material or is not intended to be retrievable, the ends of grappling hooks 26, 28, 30, 32, 34 and 36 may further include a barb to maintain the device in the septal tissue. In some embodiments, the grappling hook members 20 and 22 serve as tissue scaffolds, and are covered with a vascular material, such as polyester, biological tissue, bioresorbable polymer, or spongy polymeric material.

As shown in FIG. 3, the closure device will conform, at least to some extent, to the septal tissue that it compresses. The extent of this conformance depends upon the material from which the device was formed: a device formed of a spring metal or shape memory material will conform to the surrounding septal tissue to a lesser extent than one formed of a flexible, bioabsorbable polymer material.

Figure 4:
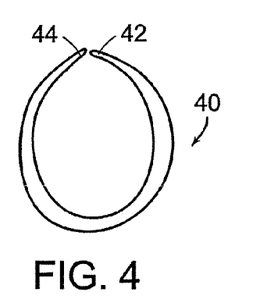
FIG. 4 is a view in side elevation of a second embodiment of the PFO closure device with mechanical anchors of the present invention.
Figure 5A:
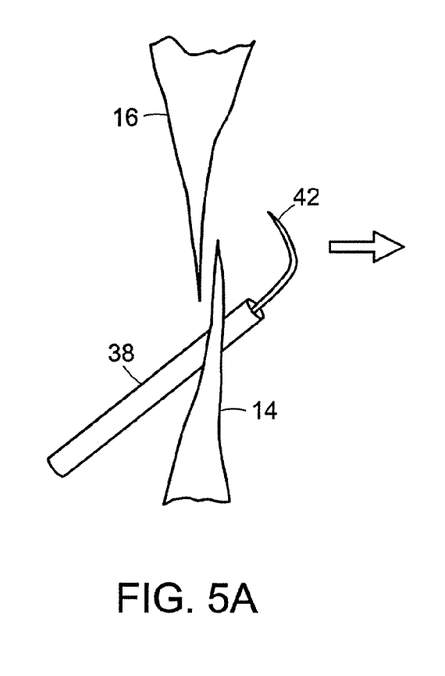
FIGS. 5a, 5b and 5c illustrate the steps in the deployment of the PFO closure device of FIG. 4.
Figure 5B:
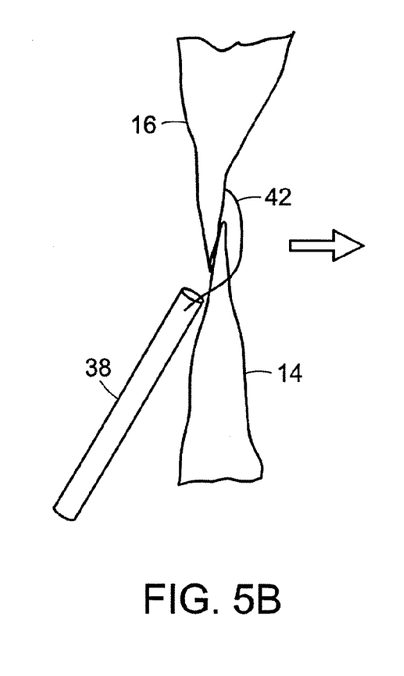
Figure 5C:
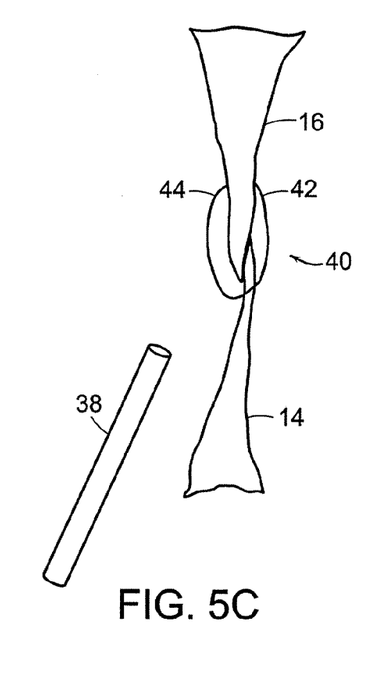

FIG. 4 shows a second embodiment of a PFO closure device with mechanical anchors indicated generally at 40. This device, when deployed, forms a ring hook design that terminates in two opposed, pointed ends 42 and 44. The device may be straightened to pass through a catheter 38. To deploy the device as shown in FIGS. 5a, 5b and 5c, the catheter is caused to pierce septum primum 14 and enter the left atrium where the pointed end 42 is deployed. Then, as shown in FIG. 5b, the catheter is drawn back through septum primum to draw the device through septum primum and embed the pointed end 42 in the left side of septum secundum. Finally, as shown in FIG. 5c, the catheter is withdrawn to fully deploy the PFO closure device and the pointed end 44 is embedded in the right side of septum secundum to compress septum primum and septum secundum together. As shown in FIGS. 4 and 5, the ring PFO closure device 40, when deployed, may include a gap that is slightly smaller than the thickness of septum secundum into which it is embedded. In some embodiments, the opposed ends 42 and 44 of the deployed PFO closure device 40 contact each other or overlap.

Figure 13:
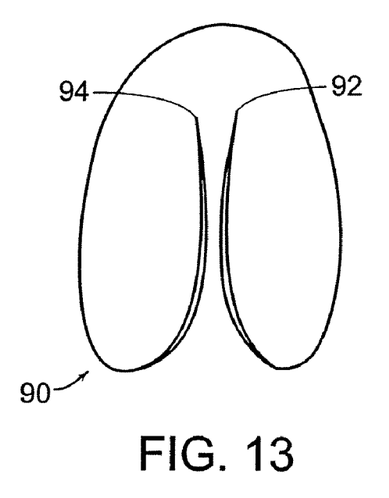
FIG. 13 is a view in side elevation of an alternative structure of the second embodiment of the PFO closure device with mechanical anchors of the present invention.
Figure 14:
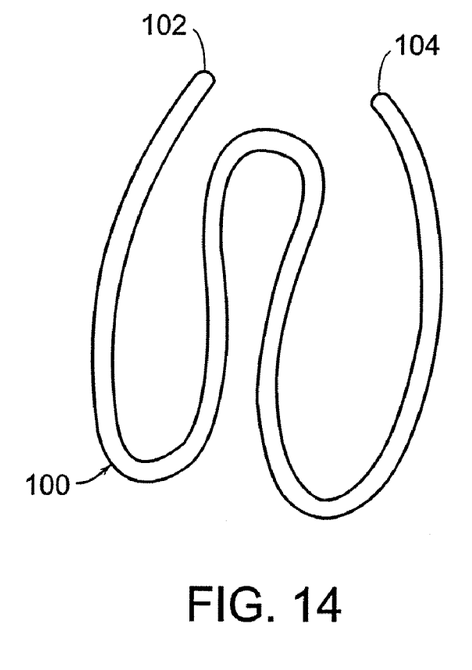
FIG. 14 is a view in side elevation of an alternative structure of the second embodiment of the PFO closure device with mechanical anchors of the present invention.
Figure 15A:
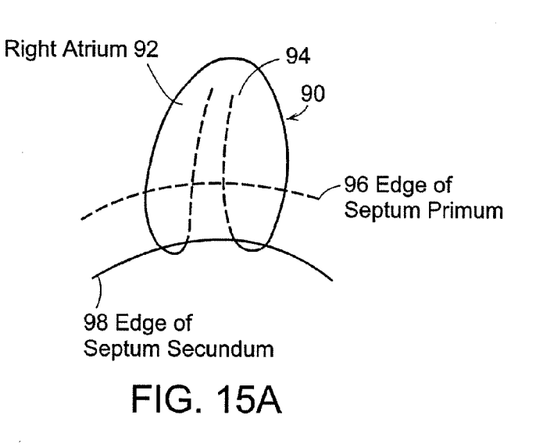
FIGS. 15a, 15b, and 15c are an end face view from the right atrium, an end face view from the left atrium, and a side elevation view, respectively, of the deployed alternative structure of the second embodiment of the PFO closure device with mechanical anchors of the present invention.
Figure 15B:
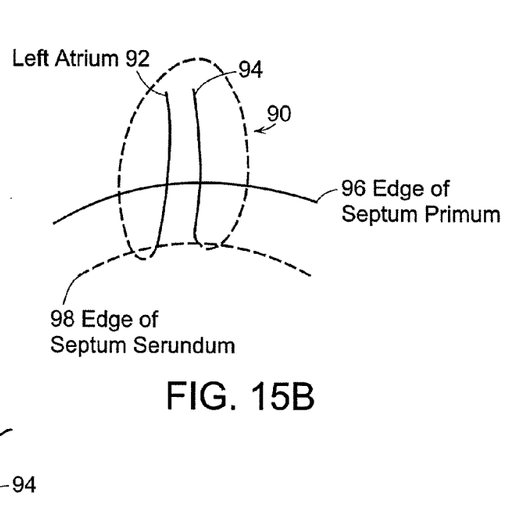
Figure 15C:
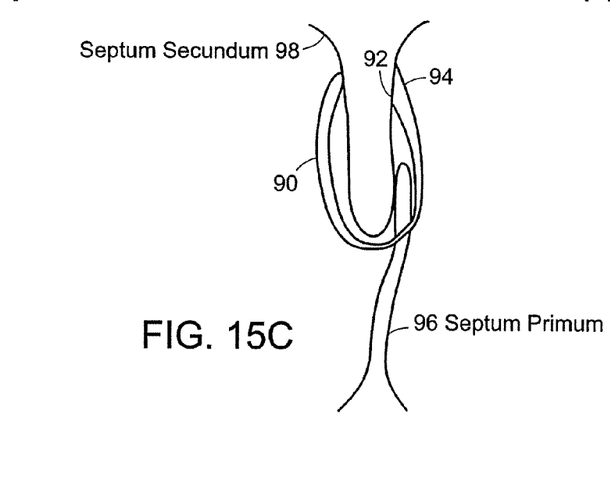

As shown in FIGS. 13 and 14, closure device 40 may take alternative forms. For example, closure devices 90 and 100 are formed as partial rings terminating in two pointed ends 92 and 94 or 102 and 104 and having at least one fold therebetween. Closure devices 90 and 100 are deployed in a manner similar to that described above and shown in FIG. 5. When deployed, the pointed ends 92 and 94 or 102 and 104 puncture the surface of septum secundum exposed in the left atrium and at least one of the folds contacts the surface of septum secundum exposed in the right atrium (FIGS. 15a and 15b). Septum primum and septum secundum are thus compressed between the pointed ends and at least one of the folds of the device (FIG. 15c).

Multiple PFO closure devices 40, 90 or 100 can be inserted until the physician is satisfied with the resultant PFO closure. Again, the PFO closure devices may be formed of flexible, bioabsorbable polymer material, spring metal, other spring-like non-bioabsorbable material, or shape memory material. The choice of material will affect the degree to which the device conforms to the surrounding septal tissue. As shown in FIGS. 4, 13, and 14, the PFO closure device may be a monolithic structure.

Figure 6:
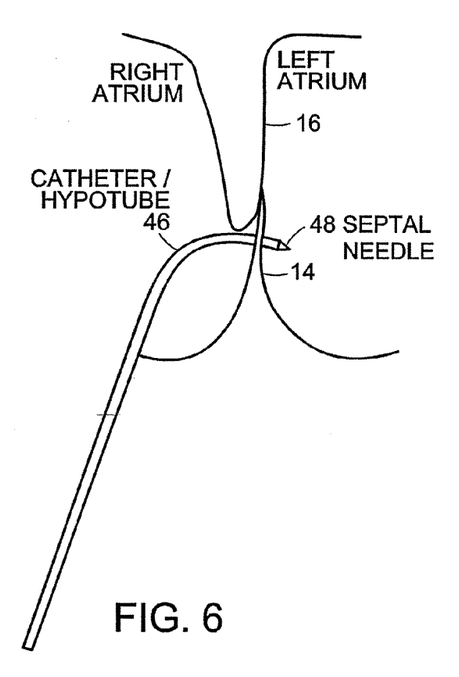
FIG. 6 is a view in side elevation of a catheter and septal puncture needle used to pierce septum primum.
Figure 7:
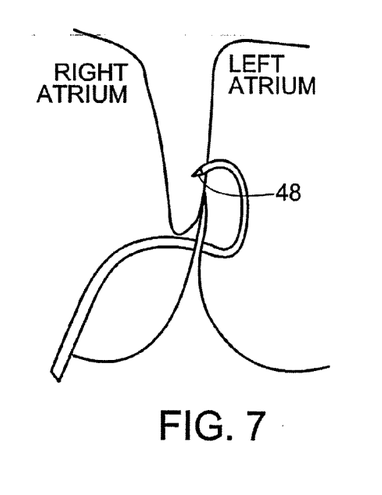
FIG. 7 is a view in side elevation of a needle anchor for PFO closure.
Figure 8:
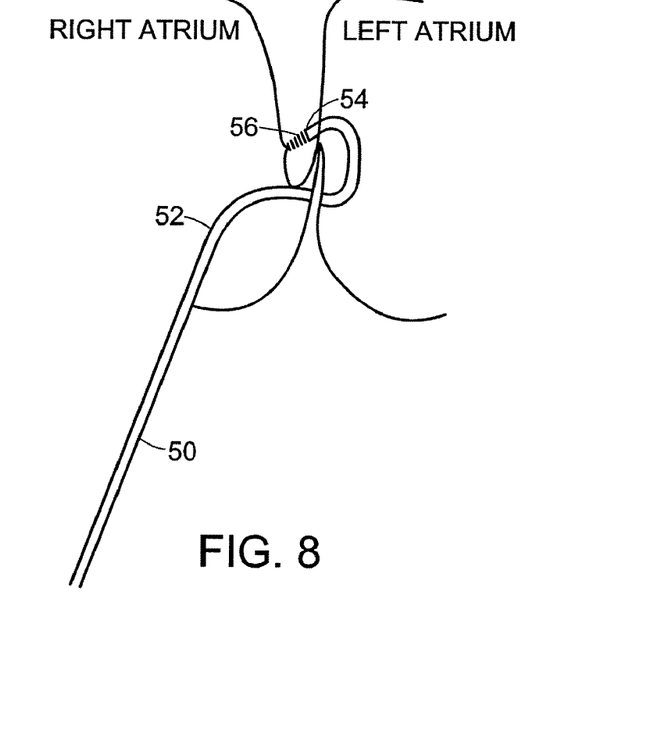
FIG. 8 is a view in side elevation of a suture and anchor used for PFO closure.

A PFO may also be closed with one or more sutures. As used in the art and indicated in the Figures, "suture" refers to a single connection used to hold two pieces of material or tissue together and need not be a continuous stitch. However, to suture a PFO closed has conventionally required the attachment of septum secundum to septum primum with a continuous stitch. This need for a continuous stitch can be eliminated by implanting sutures across the PFO using implantable suture anchors. As shown in FIGS. 6 and 7, a catheter 46 is used to puncture septum primum and then septum secundum. In the case of septum primum, the puncture creates a hole through which the catheter can pass; in the case of septum secundum, the puncture may be a depression that does not pass through septum secundum. A single puncture may be made in septum secundum as shown in FIGS. 6–8, or, as subsequently described and shown in FIG. 9, multiple punctures may be made. These punctures are made using a sharp pointed needle tip 48. Following puncture to a desired depth, the catheter 46 surrounding the needle 48 is withdrawn and the needle component returns (most likely via shape memory) to its predetermined anchor-shape.

The anchors are most likely fabricated from a shape memory alloy, such as nitinol, although they could be made from a flexible, bioabsorbable polymer or a noble metal, each having their own advantage—no long term implant issues with bioabsorbable anchors and excellent radiopacity with anchors fabricated from a noble metal, such as platinum-iridium. The remainder of the suture may be formed of any suitable material, including wire, polymeric materials, and bioabsorbable materials.

The suturing method includes using a standard septal puncture technique to locate and puncture septum primum. Following this, several approaches exist. One would be that the septal puncture needle would be withdrawn from the catheter and the suturing system then delivered through the catheter (the septal needle catheter would maintain position across septum primum during the exchange). Alternatively, a wire could be placed through the septal needle catheter to maintain position and the suture system could be delivered over the wire, or the septal puncture needle could become part of the suture system. Following delivery of the suture system, the proximal end of the suture may then be tied off so as to secure the system in place and keep the PFO closed. As described below for the rivet design suture system and shown in FIG. 10c, the proximal end of the suture may be formed into a knot, i.e. the end of the suture may be formed into a structure having a diameter larger than that of the catheter used to puncture septum primum so as to ensure that the suture system remains in place. Other suitable structures for the proximal end of the suture include, but are not limited to, coils, spirals, and other adjustable mechanisms. This structure should apply sufficient compression to hold septum primum and septum secundum together. The structure may be adjustable, such that the level of compression may be altered as necessary. Multiple sutures may be inserted until the physician is satisfied with the PFO closure.

In FIG. 8, a suture 50 is delivered through the septal needle catheter following the removal of the needle. A suture catheter 52 enters the left atrium through the septal needle catheter, is pulled back against septum secundum, setting the needle tip(s) 54 deep within it or through it, if it is thin enough. The tip could be either radiopaque, echogenic, or both, to be visible by x-ray (fluoroscopy) and/or cardiac echo. Once proper position is determined, the constricting system (a hypotube or a series of con-axial hypotubes in the embodiment where multiple needles are simultaneously delivered) is withdrawn, allowing the suture anchor 56 to form into a pre-determined shape tissue anchor, most likely via shape memory properties. The anchor 56 on the end of the suture 50 has been embedded in septum secundum and expands to anchor the suture, which passes through septum primum once the suture catheter is removed. The anchor shape can be one of many different options, including but not limited to a coil, hook, corkscrew, or grappling hook.

In those cases where a true puncture through septum secundum can be made, an anchor can be placed entirely in the right atrium, leaving nothing but suture in the left atrium. These anchors may be short strips or cylindrical rods made from a metallic or polymeric material that is biostable or bioabsorbable, or a piece of swellable foam, such as Ivalon.

Figure 9:
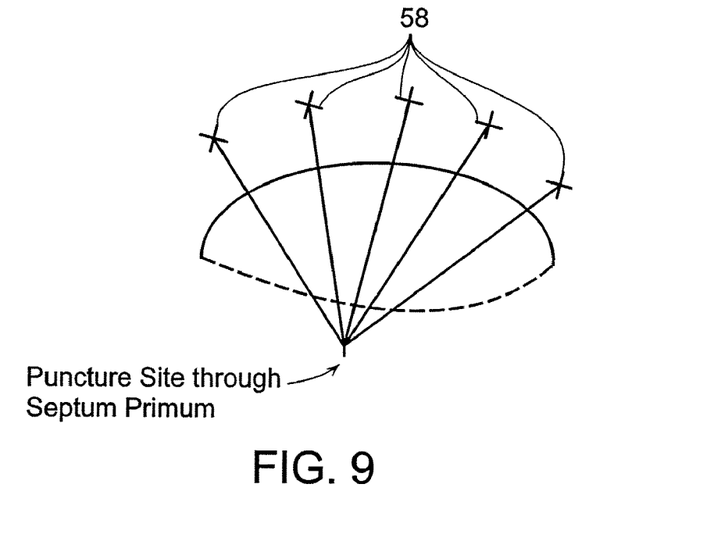
FIG. 9 is a diagram of multiple anchor placement for PFO closure.

In another embodiment, the septal needle catheter crosses septum secundum in multiple locations simultaneously. In this embodiment, the final result, as seen from the left atrium in an end face view of septum primum and septum secundum, would be as shown in FIG. 9, where a plurality of spaced anchors 58 engage septum secundum.

Figure 10A:
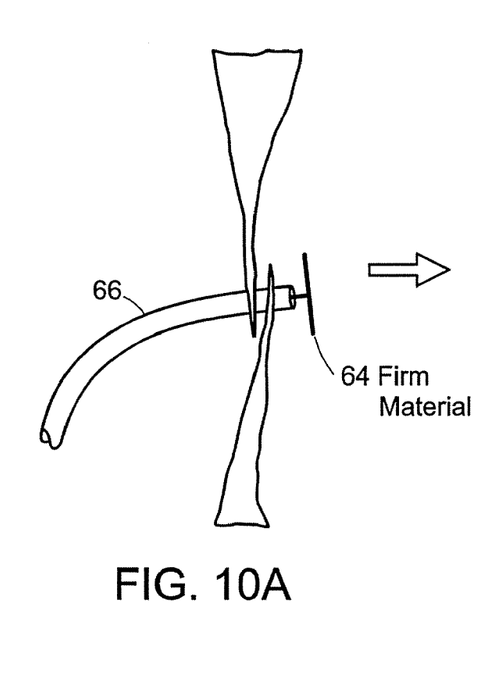
FIGS. 10a, 10b and 10c illustrate the steps in the deployment of a rivet and suture type of PFO closure device.
Figure 10B:
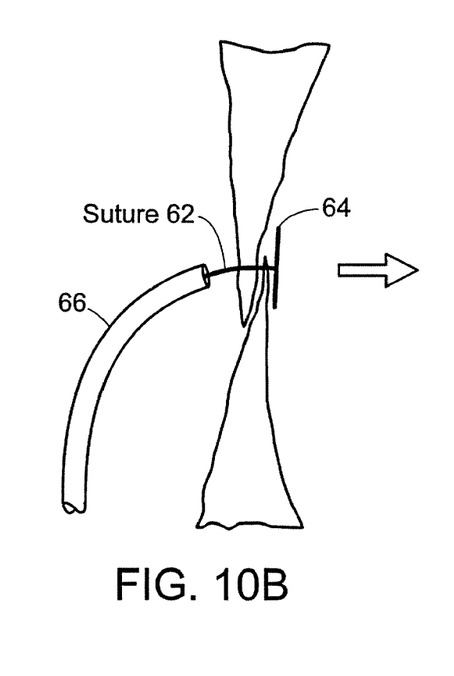
Figure 10C:
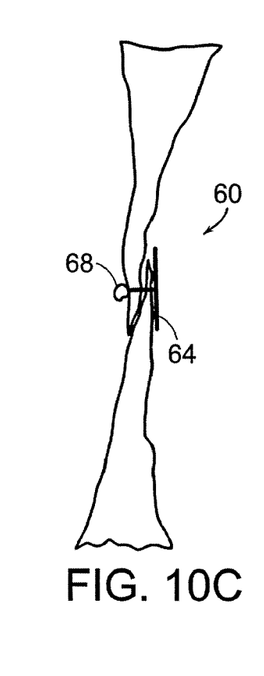

A rivet design suture system 60 is shown in FIGS. 10a, 10b and 10c. Here a suture 62 and anchor 64 are contained within a catheter 66, which pierces both septum secundum and septum primum. The anchor 64, which is formed of a firm material, such as a metal disc, a small hook (such as the shape memory hooks previously described), or a piece of bio-absorbable polymer, is then deployed into the left atrium, and the suture 62 and catheter 66 are then pulled back as shown in FIG. 10b to compress the two septa together. The suture 62 can then be knotted with knot 68, as shown in FIG. 10c, to secure the system 60 in place to keep the PFO closed, i.e. the end of the suture may be formed into a structure having a diameter larger than that of the catheter used to puncture septum primum so as to ensure that the suture system remains in place. Other suitable structures for the second end of the suture include, but are not limited to, coils, spirals, other adjustable mechanisms. As shown in FIG. 10c, this structure should apply sufficient compression to hold septum primum and septum secundum together. The structure may be adjustable, such that the level of compression may be altered as necessary. Multiple rivet systems can be inserted until a physician is satisfied with the PFO closure.

The PFO closure device of the present invention may be formed in a manner to facilitate removal once septum primum and septum secundum are fused. An exemplary removable PFO closure device 70 is deployed in the manner illustrated by FIGS. 11a–11d. The PFO closure device 70 may be delivered by a delivery catheter or sheath 72 and includes a grappling hook member 74 joined to a curved arm 76 by an enlarged tip joinder member 78. At least one of the grappling hook member and curved arm of the PFO closure device may be curved relative to the other. An elongate tether 80 is connected to the tip joinder member 78 and extends back through the catheter 72. The tether 80 can be coated to minimize trauma to the veins.

Figure 11A:
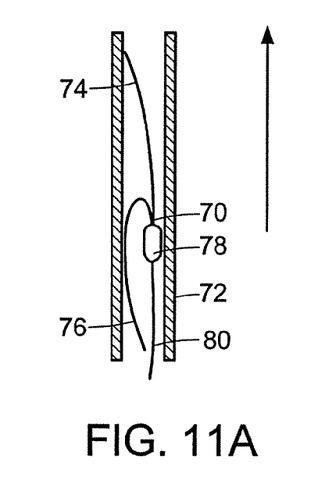
FIGS. 11a, 11b, 11c and 11d illustrate the steps in the deployment of a removable PFO closure device.
Figure 11B:
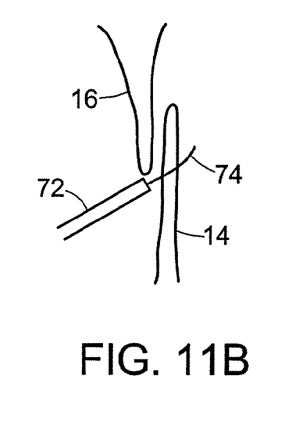
Figure 11C:
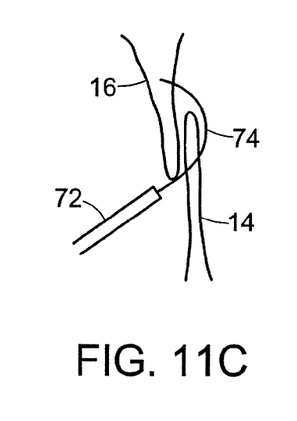

To deploy the removable PFO closure device 70 according to one embodiment of the invention, the grappling hook member 74 is passed through septum primum 14 (FIG. 11b), and the grappling hook, when free of the catheter, curves in a manner convex relative to the surface of septum secundum and penetrates septum secundum 16 (FIG. 11c). Then, the grappling hook is drawn back toward the catheter by the tether 80 to apply tension to the tissue causing septum secundum to be drawn into contact with septum primum. Then the curved arm 76 is deployed (FIG. 11d) and curves in a manner concave relative to septum secundum so as to engage septum secundum as the catheter is drawn back. The compressive force applied by the grappling hook and the curved arm hold septum primum and septum secundum tightly together. The grappling hook 74 and curved arm 76 are preferably formed of shape memory material, such as nitinol, so that they respond to body temperature when deployed from the catheter 72 to form the shape shown in FIG. 11d.

Figure 11D:
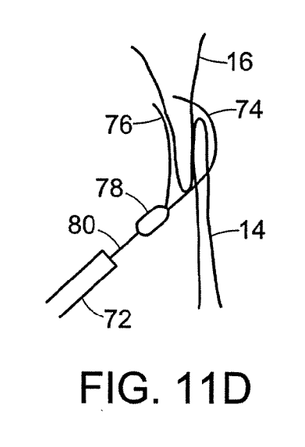
Figure 12A:
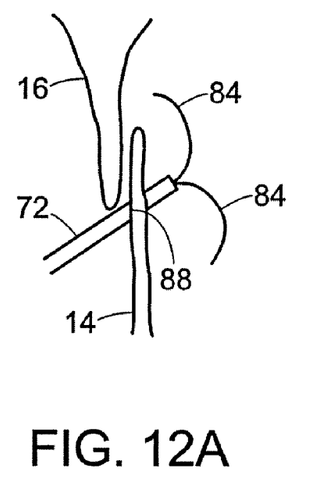
FIGS. 12a, 12b and 12c illustrate the steps in the deployment of a multiple hook PFO closure device.
Figure 12B:
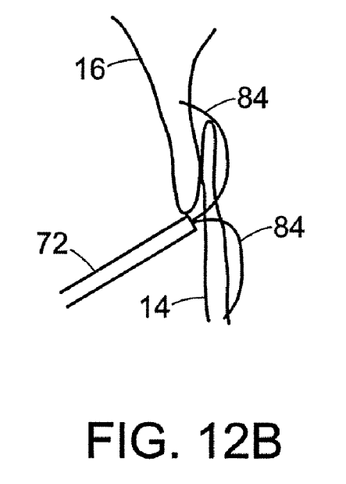
Figure 12C:
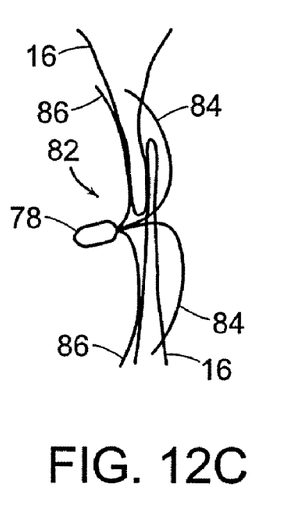

Once the PFO closure device 70 is in place, the catheter 72 is withdrawn and the free end of the tether 80 is attached to a button subcutaneously and allowed to remain in place for a period of time sufficient to allow the two septa to fuse together. Then the device is pulled through septum primum and into a recovery sheath by means of the tether 80 and removed.

What is claimed is:

1. A method of closing septum primum and septum secundum in a mammalian heart, comprising:
   (a) inserting a closure device into a right atrium of said heart, said device including first and second ends;
   (b) puncturing septum primum and passing said first end of said first end of said closure device through septum primum into a left atrium of said heart;
   (c) puncturing septum secundum with said first end of said closure device after said closure device has passed through septum primum; and
   (d) positioning said second end of said closure device against septum secundum in the right atrium such that said closure device provides a compressive force to compress at least one of septum primum and septum secundum therebetween.

2. The method of claim 1, wherein said closure device is delivered with a catheter that includes a septal puncture needle capable of puncturing mammalian tissue.

3. The method of claim 2, wherein puncturing septum secundum includes puncturing so that said first end is embedded in and does not extend through septum secundum.

4. The method of claim 3, wherein said puncturing includes the septal needle catheter puncturing septum secundum in multiple locations simultaneously, the method further comprising embedding a plurality of pieces of the closure device in septum secundum.

5. The method of claim 2, wherein puncturing septum secundum includes completely puncturing septum secundum so that said first end extends into the right atrium.

6. The method of claim 5, wherein said puncturing includes the septal needle catheter puncturing septum secundum in multiple locations simultaneously, the method further comprising deploying a plurality of pieces of the closure device into the right atrium.

7. The method of claim 1, wherein said puncturing septum primum and passing a portion of said closure device through septum primum constitutes one step.

8. The method of claim 1, wherein said puncturing septum primum and passing a portion of said closure device through septum primum constitutes two steps.

9. The method of claim 1, wherein said first end of said closure device includes a shape memory material.

10. The method of claim 9, wherein said shape memory material includes nitinol.

11. The method of claim 1, wherein said closure device is formed of a material selected from the group consisting of bioresorbable materials, noble metals, shape memory materials, metals, polymeric materials, or swellable foams.

12. The method of claim 1, wherein said first end is formed into a coil, hook, corkscrew, or other anchor.

13. The method of claim 1, wherein said second end is formed into a knot, coil, spiral, or other adjustable mechanism sufficient to hold said closure device in place.

14. The method of claim 1, wherein said second end of said closure device has a structure that is adjustable to alter the compressive force applied to septum primum and septum secundum.

15. The method of claim 1, wherein steps (a) through (d) are repeated at least once for multiple closure devices.

16. The method of claim 1, wherein said closure device is shaped as a ring with a gap, the ring being positioned so that said first end punctures and embeds into said septum secundum on the left atrium side and said second end punctures and embeds into said septum secundum on the right atrium side, said septum secundum being compressed in said gap.

17. The method of claim 16, wherein said ring consists of a single monolithic piece.

18. The method of claim 16, wherein said inserting includes providing the closure device in a catheter, said closure device being elongated so that the gap between said first and second ends is enlarged.

19. The method of claim 1, wherein said closure device is shaped as a ring with first and second ends and at least one fold therebetween, said ring being positioned so that said first and second ends puncture septum secundum on the left atrium side and said at least one fold contacts septum secundum in the right atrium, septum secundum being compressed between said first and second ends and said at least one fold.

20. The method of claim 1, wherein the device has a first piece including said first end, and a separate second piece including said second end, said first and second pieces connected together at a location in the right atrium, at least one of said pieces being curved relative to the other said piece.

21. The method of claim 20, wherein said first piece is convex relative to septum secundum and said second piece is concave relative to septum secundum.

22. The method of claim 20, further comprising retrieving and removing said closure device after it has been deployed.

23. The method of claim 1, further comprising retrieving and removing said closure device after it has been deployed.

24. The method of claim 1, wherein said closure device includes a grappling hook member joined to at least one curved arm by an enlarged-tip joinder member, said grappling hook member is connected to an elongate tether, said grappling hook member including at least one grappling hook capable of being reversibly and distally elongated, wherein puncturing septum secundum includes deploying said grappling hook member such that said at least one grappling hook is embedded into the surface of septum secundum in the left atrium, applying tension to said tether such that said grappling hook draws septum secundum into contact with septum primum, and said positioning includes deploying said at least one curved arm such that said curved arm engages the surface of septum secundum exposed in the right atrium.

25. The method of claim 24, wherein said grappling hook member includes a plurality of grappling hooks and, upon deploying said grappling hook member in the left atrium, said plurality of grappling hooks are embedded in the surfaces of both septum primum and septum secundum in the left atrium.

26. The method of claim 25, wherein said closure device includes a plurality of curved arms and, upon deployment in the right atrium, said plurality of curved arms engage both the surfaces of septum primum and septum secundum exposed in the right atrium.

27. The method of claim 24, wherein said inserting includes providing the closure device in a catheter, said closure device being elongated such that said first and second ends are distally elongated relative to said joinder member.

28. The method of claim 24, further comprising retrieving said closure device after a period of time sufficient to allow septum primum and septum secundum to fuse together by grabbing said joinder member with a removal device and withdrawing said grappling hook member of said closure device through septum primum.

29. The method of claim 24, further comprising withdrawing said catheter from said heart and attaching said tether to a subcutaneous button and retrieving said closure device after a period of time sufficient to allow septum primum and septum secundum to fuse together by pulling said device through septum primum and into a recovery sheath by means of the tether.

* * * * *